(12) United States Patent
Bonelli et al.

(10) Patent No.: US 11,911,242 B2
(45) Date of Patent: *Feb. 27, 2024

(54) TRANSVERSELY EXTENSIBLE CONTINUOUS ELASTIC LAMINATE, AND A METHOD FOR PRODUCING THE SAME

(71) Applicant: Fameccanica.Data S.p.A., San Giovanni Teatino (IT)

(72) Inventors: Guido Bonelli, San Giovanni Teatino (IT); Gabriele Sablone, San Giovanni Teatino (IT)

(73) Assignee: Fameccanica.Data S.p.A. (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/675,227

(22) Filed: Feb. 18, 2022

(65) Prior Publication Data

US 2022/0265481 A1 Aug. 25, 2022

(30) Foreign Application Priority Data

Feb. 22, 2021 (EP) .................................... 21158338

(51) Int. Cl.
*A61F 13/15* (2006.01)
*A61F 13/49* (2006.01)
*B32B 37/14* (2006.01)
*B32B 5/04* (2006.01)
(Continued)

(52) U.S. Cl.
CPC .. *A61F 13/15593* (2013.01); *A61F 13/15699* (2013.01); *A61F 13/4902* (2013.01); *B32B 5/04* (2013.01); *B32B 7/05* (2019.01); *B32B 37/14* (2013.01); *B32B 38/0004* (2013.01); *B32B 38/1875* (2013.01); *A61F 2013/49033* (2013.01); *B32B 2307/51* (2013.01); *B32B 2555/02* (2013.01)

(58) Field of Classification Search
CPC .......... A61F 13/15577; A61F 13/15593; A61F 13/153699; A61F 13/15739; A61F 13/15756; A61F 13/15764; A61F 2013/15861; A61F 2013/49033; A61F 13/15699; A61F 13/4902; B32B 38/0004; B32B 38/1875; B32B 2307/51; B32B 2555/02
See application file for complete search history.

(56) References Cited

U.S. PATENT DOCUMENTS

| | | | |
|---|---|---|---|
| 2005/0215963 A1* | 9/2005 | Autran | A61F 13/49015 604/385.27 |
| 2017/0252229 A1* | 9/2017 | Bonelli | A61F 13/49014 |
| 2022/0265482 A1* | 8/2022 | Bonelli | B32B 37/14 |

FOREIGN PATENT DOCUMENTS

EP 3213728 A1 9/2017

OTHER PUBLICATIONS

European Search Report dated Aug. 18, 2021. 4 pages.

* cited by examiner

*Primary Examiner* — Humera N. Sheikh
*Assistant Examiner* — Kevin Ct Li
(74) *Attorney, Agent, or Firm* — RMCK Law Group PLC (57) ABSTRACT

A transversally extensible elastic laminar web including a support web having a continuous edge portion sandwiched between two corresponding edge portions of two overlapped webs and a plurality of tabs extending from the edge portion outside the two overlapped webs, wherein each tab has a respective micro-hook pad fixed to a planar surface, and wherein the planar surface of each tab has a portion which completely surrounds the respective micro-hook pad.

14 Claims, 6 Drawing Sheets

(51) Int. Cl.
*B32B 7/05* (2019.01)
*B32B 38/00* (2006.01)

fig.1 fig.2 fig.3 fig.4 fig.5 fig.6 fig.7 fig.8 fig.9 fig.10 fig.11 fig.12 fig.13 fig.14

TRANSVERSELY EXTENSIBLE CONTINUOUS ELASTIC LAMINATE, AND A METHOD FOR PRODUCING THE SAME

CROSS-REFERENCE TO RELATED APPLICATION

This application claims priority to European Patent Application No. 21158338.0 filed Feb. 22, 2021. The disclosure of the above application is incorporated herein by reference in its entirety.

FIELD OF THE INVENTION

The present invention relates to a transversely extensible continuous elastic laminate.

The present invention has been developed with particular reference to the production of disposable absorbent sanitary articles, such as, for example, diapers, training pants, absorbent sanitary products for incontinent adults, etc.

A transversely extensible continuous elastic laminate may constitute a semi-finished intermediate product which can be used for supplying machines for manufacturing absorbent sanitary articles. The transversely extensible continuous elastic laminate can be cut transversely to produce elastic side panels for absorbent sanitary articles. Discrete left and right fastening tabs could be already attached externally on the elastic laminate.

Embodiments of the present invention also relate to elastic side panels for absorbent sanitary articles.

The present invention also relates to a method for producing a transversely extensible continuous elastic laminate.

PRIOR ART

An absorbent sanitary article wearable as a pant typically has a structure that comprises a rectangular-shaped central body or chassis and at least one pair of side panels which extend laterally from opposite sides of the central body in the front or rear section of the central body. The side panels are provided with fastening tabs, typically comprising micro-hooks pads, which can be releasably attached to a web for closing the absorbent sanitary article around the waist of the user. The side panels of an absorbent sanitary article are usually elastically extensible.

Elastic side panels, due to the function that they perform—namely to maintain the absorbent article closed around the waist of the user—are subject to high stresses which can easily lead to breaking the joint between the elastic portions of the side panels and the fastening tabs carrying the micro-hooks pads.

EP-A-3213728 discloses a transversely extensible elastic laminate comprising: a first and a second web, having respective pleated central portions, an elastic tape sandwiched between the pleated central portions of the first and second web and elastically stretchable in a transverse direction, and a plurality of fastening tabs spaced apart from each other in a longitudinal direction. The fastening tabs each include a rectangular support web and a micro-hook pad fixed at a distal end of the rectangular support web.

A first drawback of this prior art solution is that the fastening tabs are connected to the first and second web along a relatively small area. When the user pulls the fastening tab, the stress is distributed only to a limited area of the elastic portion of the side panel, which increases the risk of breaks.

A second drawback of this known solution is that the micro-hook fastening pads extend for the whole width of the support tape, i.e., the lateral edges of the micro-hook pads are aligned to the lateral edges of the support web. When touching the fastening tab, the user perceives a sharp feeling due to the fact that the rigid micro-hook pads extend up to the edges of the fastening tab. This structure of the fastening tabs gives rise to an unpleasant stiffness and sharpness perception during the application of the sanitary article to the wearer. It is not unusual that the user gets scratches or small cuts on the soft skin under the nails due to the contact with sharp and rigid edges of the micro-hook pads.

Regarding the manufacturing method, in the prior art the fastening tabs are supplied as discrete elements set at a constant pitch, which requires complex and expensive apparatuses.

OBJECT AND SUMMARY OF THE INVENTION

The object of the present invention is to overcome the drawbacks of the prior art outlined above.

According to a first aspect of the invention, this object is achieved by a transversely extensible continuous laminate having the features of claim 1.

The transversely extensible continuous laminate can be collected in reels which can be used for supplying machines for manufacturing absorbent sanitary articles. The fact that the transversely extensible laminates for producing the elastic side panels are supplied to the manufacturing machines in a ready-to-use form simplifies considerably the manufacturing machines, which do not need to include all the apparatus, devices and components necessary for the in-line manufacturing of the elastic side panels, which are a substantial part of the machines for manufacturing absorbent sanitary products. This also involves substantial energy savings, which have a positive impact on the sustainability of the manufacturing process.

According to another aspect, the present invention relates to an elastic side panel for absorbent sanitary articles having the features of claim 5.

According to another aspect, the invention relates to a method for producing a transversely extensible laminate having the features of claim 10.

The manufacturing method as compared to the prior art provides a better control on the distance between the fastening tabs, which in the method according to the invention are not applied as discontinuous discrete elements. This reduces manufacturing wastes and has a direct positive impact on sustainability.

The claims form an integral part of the technical disclosure provided here in relation to the invention.

BRIEF DESCRIPTION OF THE DRAWINGS

The present invention will now be described with reference to the attached drawings, provided purely by way of non-limiting example, wherein.

In the following description, identical or similar components will be indicated by the same reference numerals.

It should be appreciated that the attached drawings are schematic and not to scale with respect to real products. Various figures may not be represented in the same scale. Also, in various figures some elements may not be shown to better show other elements.

DETAILED DESCRIPTION

FIGS. 1-6 schematically show various steps for producing a transversely extensible continuous elastic laminate.

Figure 1:
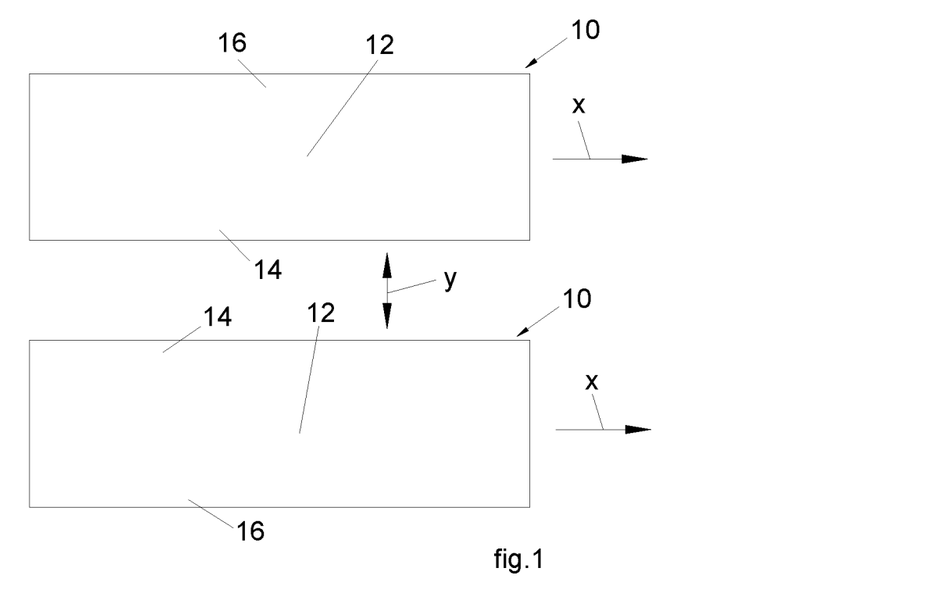
FIGS. 1-6 are schematic plan views showing various steps of a method for producing a transversely extensible continuous elastic laminate having integrated micro-hook fastening elements.

In a first step, shown in FIG. 1, two first continuous webs 10 are fed in a longitudinal direction X. The two first continuous webs 10 may be made of a non-woven material. In a possible embodiment, the two first continuous webs 10 may be obtained from a single continuous web unwound from a reel and cut longitudinally so as to form two separate webs advancing in the longitudinal direction X.

The two first continuous webs 10 are spaced apart from each other in a transversal direction Y orthogonal to the longitudinal direction X.

Each of the two first continuous webs 10 has a central portion 12 and first and second edge portions 14, 16 opposite to each other with respect to the central portion 12.

The two first continuous webs 10 may be positioned on the outer surface of a wheel or on the upper surface of a conveyor belt as they advance continuously in the longitudinal direction X.

Figure 2:
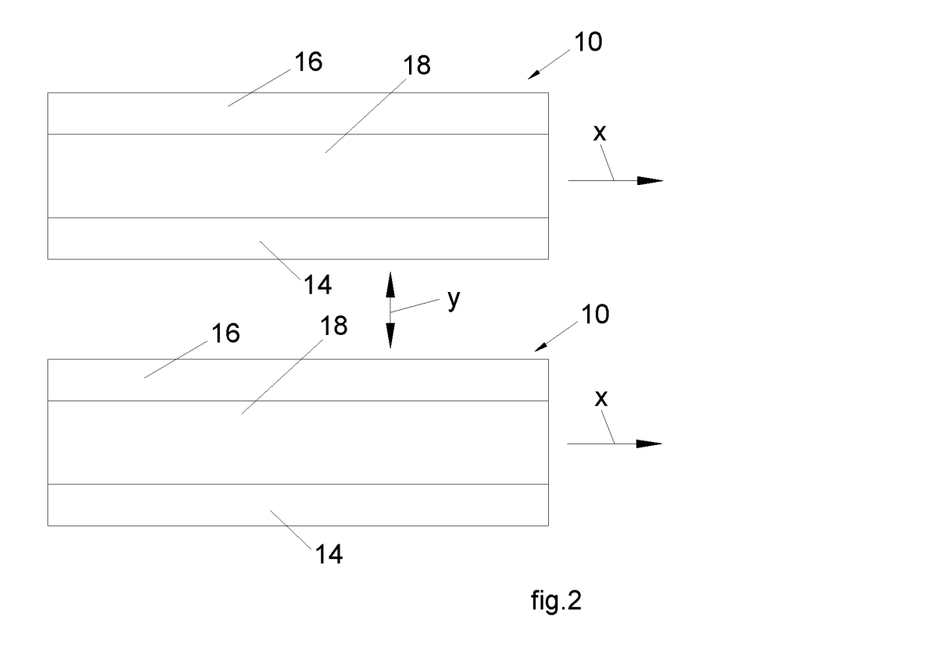

In a second step, shown in FIG. 2, two continuous elastic tapes 18 are fed in the same longitudinal direction X and are overlapped to the respective central portions 12 of the two first continuous webs 10. The two elastic tapes 18 may be obtained from a single continuous elastic tape unwound from a reel and cut longitudinally so as to form the two separate elastic tapes advancing in the longitudinal direction X.

The two elastic tapes 18 are elastically stretched in the transversal direction Y when they are applied to the respective central portions 12 of the two continuous webs 10. The two continuous elastic tapes 18 may have the capability to extend in the transversal direction Y by at least 100%, and preferably by 300%, with respect to the respective rest dimensions and to return to the respective rest dimensions in the absence of a transversal force. In a possible embodiment, the degree of transversal elastic stretching of the two continuous elastic tapes 18 may be in the order of 200%. This means that the two continuous elastic tapes 18 are applied on the respective first continuous webs 10 with a width essentially equal to three times the width that the continuous elastic tapes 18 have at rest, i.e., in the absence of transversal forces.

The transverse extension of the two continuous elastic tapes 18 may be obtained by a spreading device comprising, for each continuous elastic tape 18, two wheels with respective axes inclined with respect to each other, as disclosed in EP-A-3213728.

The transversely stretched continuous elastic tapes 18, once applied to the respective central portions 12 of the two first continuous webs 10 may be retained in the stretched state by vacuum suction, as disclosed in EP-A-3213728.

In a possible embodiment, the continuous elastic tapes 18 may have different widths in the transverse direction Y and/or may be stretched in said transverse direction Y to reach different widths.

Figure 3:
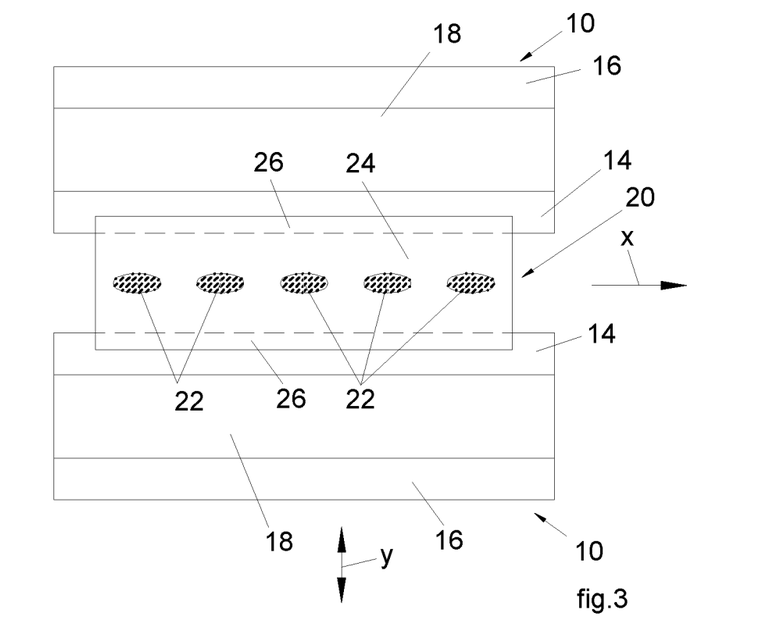

With reference to FIG. 3, the method comprises providing a continuous support web 20 having a row of micro-hook pads 22 fixed to a planar surface 24 of the support web 20. The continuous support web 20 has two continuous longitudinal edge portions 26. The continuous support web 20 may be made of a non-woven material.

The row of micro-hook pads 22 is located in a central portion of the support web 20. The micro-hook pads 22 are spaced apart from each other in the longitudinal direction X. The micro-hook pads 22 may be fixed to the planar surface 24 of the support web 20 by any conventional means, for instance by glue, thermomechanical welding, ultrasonic welding, etc.

In a possible embodiment, the micro-hook pads 22 may have the respective micro-hooks alternately oriented in opposite directions, so that in each pair of adjacent micro-hook pads 22 the micro-hooks of one pad 22 are oriented in a direction opposite with respect to the micro-hooks of the other pad 22.

Figure 14:
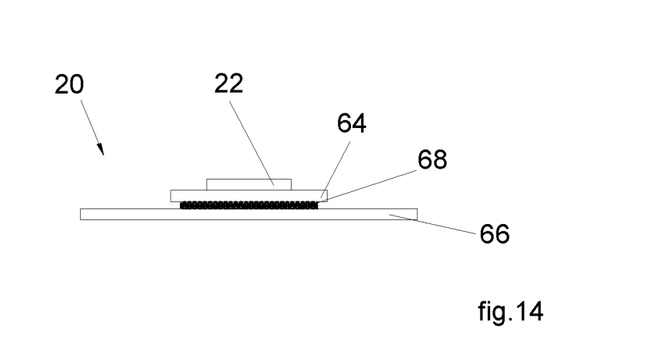
FIG. 14 is a schematic cross-section showing a possible embodiment of a continuous support web used in the method according to the invention.

With reference to FIG. 14, in a possible embodiment the continuous support web 20 may comprise a first layer 64 carrying the row of micro-hook pads 22 and a second layer 66 joined to the first layer 64, for instance by a glue layer 68. The first layer 64 should have a relatively large mechanical resistance for supporting the micro-hook pads 22 whereas the second layer 66 does not need a great mechanical resistance. Both the first layer 64 and the second layer 66 may be made of non-woven materials. This solution allows a reduction of costs, in that the more robust and more expensive first layer 64 may have reduced dimensions (it may have a width only a few millimetres greater than the width of the micro-hook pads 22) whereas the second layer 66 which can be less resistant and less expensive than the first layer 64 has a larger width. The first layer 64 with the micro-hook pads 22 fixed thereto may be manufactured by producers of web materials for absorbent sanitary articles and may be supplied in reels. In the method for producing the transversely extensible continuous elastic laminate according to the present invention, the first layer 64 and the second layer 66 may be unwound from respective reels and are joined to each other before being applied to the two first continuous webs 10 for instance by a glue layer 68. This has the additional advantage of having reels which are more compact and less subject to damages.

As shown in FIG. 3, the continuous support web 20 is fed in the longitudinal direction X and the two continuous longitudinal edge portions 26 of the support web 20 are applied to respective first edge portions 14 of the two first continuous webs 10. The two continuous longitudinal edge portions 26 of the continuous support web 20 may be retained on the respective edge portions 14 of the two first continuous webs 10 by the same vacuum suction which holds the stretched elastic tapes 18 on the first webs 10.

Figure 4:
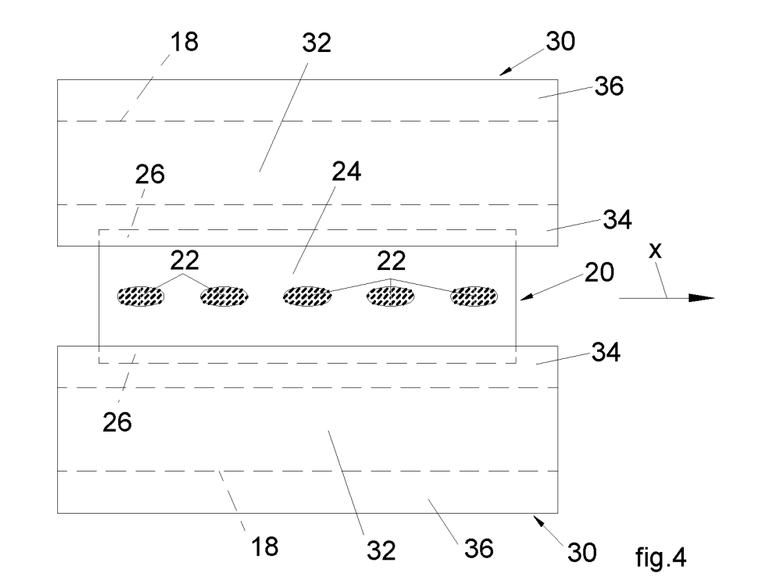

As shown in FIG. 4, in a further step two second continuous webs 30 are fed in the longitudinal direction Y, and are overlapped to the respective first continuous webs 10.

In a possible embodiment, the two second continuous webs 30 may be obtained from a single continuous web unwound from a reel and cut longitudinally so as to form two separate webs advancing in the longitudinal direction X.

The two second continuous webs 30 are spaced from each other in the transverse direction Y and have respective central portions 32 and respective first and second edge portions 34, 36 on opposite sides of the central portion 32. The two second continuous webs 30 may have the same width as the first continuous webs 10. The two second continuous webs 30 are applied over the respective first continuous webs 10 so that the two continuous elastic tapes 18 are sandwiched between the respective central portions 12, 32 of the first and second webs 10, 30. Also, the two continuous longitudinal edge portions 26 of the support web 20 are sandwiched between respective first edge portions 14, 34 of the two first and second continuous webs 10, 30.

Figure 5:
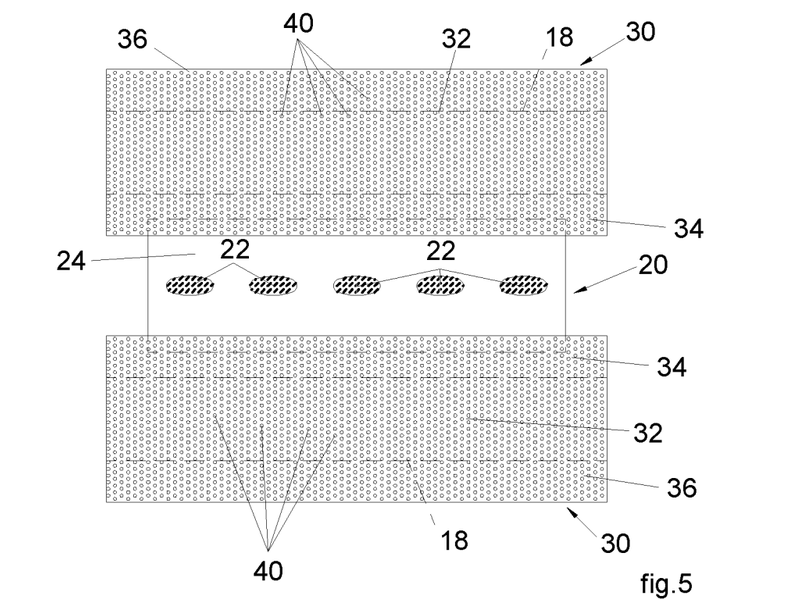

Then, as shown in FIG. 5, the two first and second webs 10, 30, the two elastic tapes 18 and the edge portions 26 of the support web 20 are fixed to each other by a pattern of spot welds 40. The spot welds 40 may be formed by ultrasonic welding as disclosed in EP-A-3213728. The pattern of spot welds 40 may have a reinforced area along the longitudinal portion connecting the first edge portions 14, 34 of the first and second webs to the edge portions 26 of the support web 20, in order to provide an increased connection strength in that area.

The elastic tapes 18 are stretched in the transversal direction Y during the spot welding which joins the elastic tapes 18 to the first and second webs 10, 30. The welding spots 40 may form through holes in the elastic tapes 18 in order to provide breathability features to the composite laminate, as disclosed in EP-A-3213728.

Figure 6:
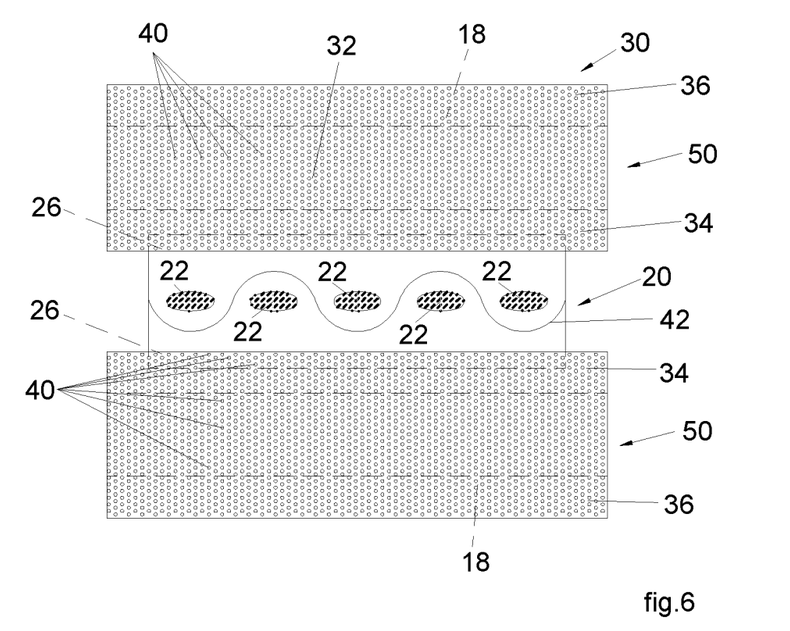

With reference to FIG. 6, the method further comprises a cutting step wherein the support web 20 is cut along one continuous undulated cutting line 42 passing between each pair of adjacent micro-hook pads 22. The continuous undulated cutting line 42 may be made by a cutting roller having a shaped cutting blade. The continuous undulated cutting line 42 is distanced from the edges of the micro-hook pads 22 so that each micro-hook pad 22 is completely surrounded by a portion of the planar surface 24 of the support web 20.

Figure 7:
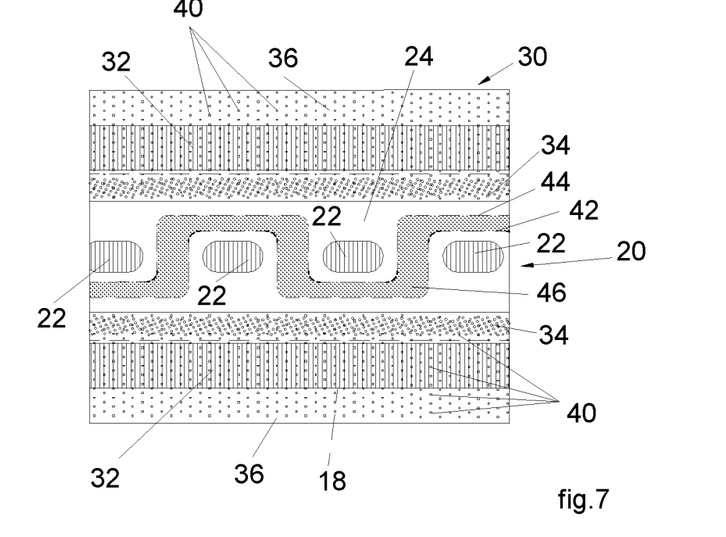
FIG. 7 is a schematic plan view showing a step of the method alternative to the step shown in FIG. 6.

As shown in FIG. 7, in a possible embodiment, the support web 20 may be cut along two continuous undulated cutting lines 42, 44 which define a continuous undulated strip 46 comprised between the two cutting lines 42, 44. The continuous undulated strip 46 is discarded as waste.

The continuous undulated cutting line 42 or the continuous undulated cutting lines 42, 44 may pass at a distance from the edges of said micro-hook pads 22 comprised between 1-10 mm and preferably comprised between 2-7 mm.

Figure 8:
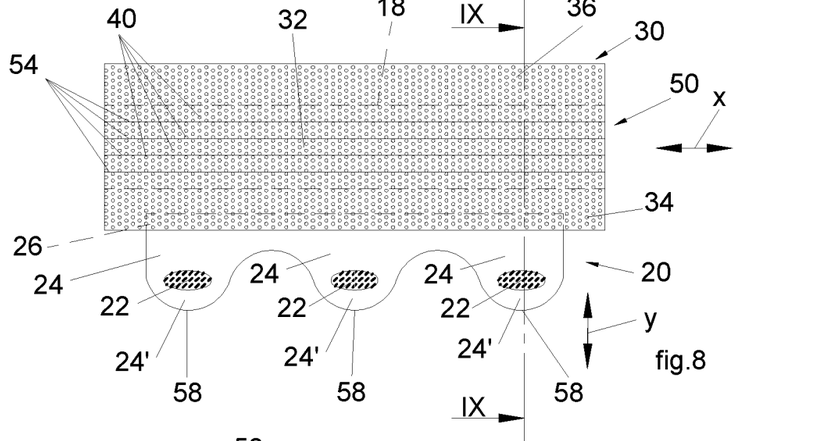
FIG. 8 is a schematic plan view of a transversely extensible continuous elastic laminate in an extended position.
Figure 9:
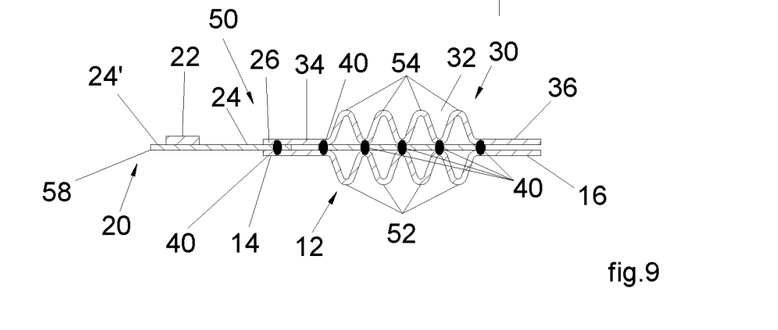
FIG. 9 is a schematic cross-section taken along the line IX-IX of FIG. 8.

After the cut of the support web 20 along the cutting line 42 or cutting lines 42, 44, two separate transversely extensible continuous elastic laminates 50 are formed, each of which has the form shown in FIGS. 8 and 9.

With reference to FIGS. 8 and 9, the transversely extensible continuous laminate 50 obtained by the previously disclosed method comprises a first and second continuous web 10, 30 extending along a longitudinal direction X and a continuous elastic tape 18 elastically extensible in a transversal direction Y and sandwiched between the central portions 12, 32 of the first and second continuous web 10, 30 and joined thereto by a pattern of spot welds 40.

When the vacuum suction which holds the elastic tape stretched in the transversal direction Y is released, the elastic tape 18 contracts in the transversal direction Y. The transversal contraction of the elastic tape 18 forms longitudinal pleats 52, 54 on the central portions 12, 34 of the first and second continuous web 10, 30. The edge portions 14, 34 and 16, 36 of the first and second continuous webs 10, 30 which extend transversally beyond the elastic tape 18 remain non-pleated.

The transversely extensible continuous elastic laminate 50 comprises a support web 20 which includes a continuous longitudinal edge portion 26 which is sandwiched between the first non-pleated edge portions 14, 34 of the first and second web 10, 30 and is fixed thereto by said pattern of spot welds 40. The pattern of spot welds 40 may be reinforced in the area connecting the first non-pleated edge portions 14, 34 of the first and second web 10, 30 and the continuous edge portion 26 of the support web 20.

The support web 20 includes a plurality of tabs 58 which extend from the continuous longitudinal edge portion 26 outside the first and second web 10, 30. The tabs 58 are connected to each other by the continuous edge portion and are spaced apart from each other in the longitudinal direction X. Each tab 58 has a respective micro-hook pad 22 fixed to a planar surface 24 of the respective tab 58. The planar surface 24 of each of the tabs 58 has a portion 24' which completely surrounds the respective micro-hook pad 22. In a possible embodiment the portion 24' of the planar surface 24 may have a width greater than 2 mm. The width of each tab 58 along a line parallel to the direction X and passing through the respective micro-hook pad 22 should be at least 4 mm larger than the width of the micro-hook pad 20 along the same line (2 mm on each side of the micro-hook pad 20). The width of each tab 58 may be 100 mm larger than the width of the micro-hook pad 20. For instance, if the width of the micro-hook pad 20 is 50 mm, the width of the respective tab 58 may be comprised between 54 mm and 150 mm.

In a possible embodiment, the support web 20 comprises a first layer 64 forming a distal portion of the tabs 58 and carrying said micro-hook pads 22 and a second layer 66 forming said continuous edge portion 26 and intermediate portions of the tabs 58 extending between said distal portion and the continuous edge portion 26. The first layer 64 and the second layer 66 are joined to each other, for instance by a glue layer 68.

Figure 10:
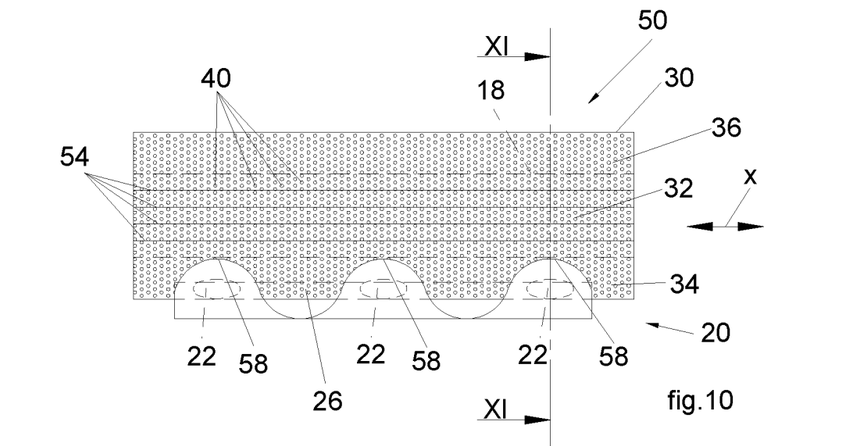
FIG. 10 is a schematic plan view showing the transversely extensible continuous elastic laminate of FIG. 8 in a folded configuration.
Figure 11:
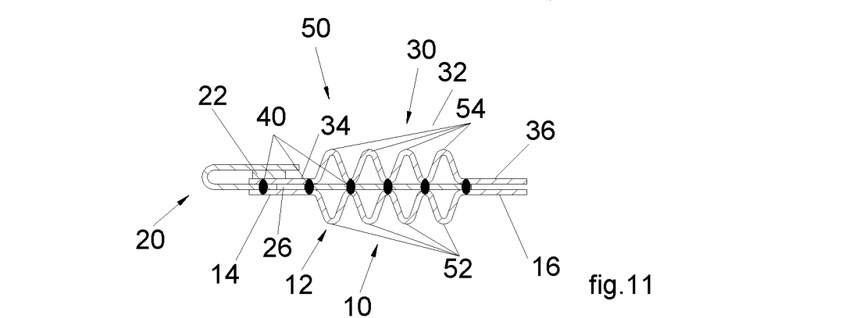
FIG. 11 is a schematic cross-section taken along the line XI-XI of FIG. 10.

With reference to FIGS. 10 and 11, the tabs 58 of the support web 20 may be folded over the second web 30 along a folding line parallel to the longitudinal axis X, so that the micro-hook pads 22 are releasably fastened to corresponding portions of the second web 30. Folding of the tabs 58 may be carried out before or after releasing the vacuum suction which keeps the elastic tape 18 stretched in the transverse direction Y. When the tabs 58 are folded as shown in FIGS. 10 and 11, the transversely extensible continuous elastic laminate 50 can be handled more easily without the risk that the micro-hook pads 22 engage with a non-woven web when the transversely extensible continuous elastic laminate 50 is wound in a reel or during the manufacturing process of absorbent sanitary products.

The transversely extensible continuous elastic laminate 50 shown in FIG. 10 can be wound in reels which can be stored and shipped to manufacturing plants. The reels containing the transversely extensible continuous elastic laminate 50 are intended to produce elastic side panels in machines for manufacturing absorbent sanitary articles.

In a possible embodiment, the transversely extensible continuous elastic laminate 50 may be formed in-line with respect to a manufacturing machine, so that the transversely extensible continuous elastic laminate 50 are supplied in-line to the manufacturing machine without being previously collected in reels.

In the machine for manufacturing absorbent sanitary products, the transversely extensible continuous elastic laminate 50 is cut along lines generally transversal to the longitudinal axis X for forming individual elastic side panels. The cutting lines which form the individual elastic side panels may have different shapes so as to form elastic side panels with the desired shape. The cuts which originate the individual elastic side panels are typically carried out while the tabs 58 of the transversely extensible continuous elastic laminate 50 are folded as shown in FIGS. 10 and 11.

Figure 12:
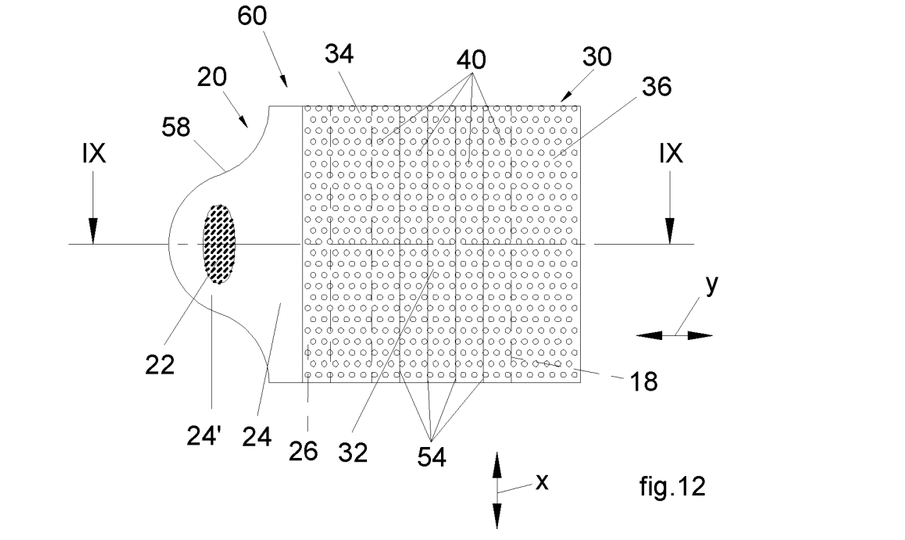
FIG. 12 is a schematic plan view showing an elastic side panel for absorbent sanitary articles in an extended position.

An individual elastic side panel obtained from a transversely extensible continuous elastic laminate 50 is shown in FIG. 12 and is indicated by the reference numeral 60. The elastic side panel 60 is shown in an extended position for a better understanding. FIG. 9, which is a cross-section taken along the line IX-IX of the transversely extensible continuous elastic laminate 50 of FIG. 8, is identical to a cross-section taken along the line IX-IX of the individual elastic side panel 60 of FIG. 12.

With reference to FIGS. 12 and 9, the elastic side panel 60 comprises a first and a second web 10, 30 having respective pleated central portions 12, 34 having respective pleats 52, 54 parallel to a first direction X, and respective first and second non-pleated edge portions 14, 34 and 16, 36 on opposite sides of the pleated central portions 12, 32. An elastic tape 18 is sandwiched between the pleated central portions 12, 32 of the first and second web 10, 30. The elastic tape 18 is elastically stretchable in a second direction Y transversal to the first direction X. The elastic tape 18 is joined to the first and second web 10, 30 by a pattern of spot welds 40.

The elastic side panel 60 comprises a support web 20 including an edge portion 26 sandwiched between the first non-pleated edge portions 14, 34 and fixed thereto by said pattern of spot welds 40. The pattern of spot welds 40 may be reinforced in the area connecting the first non-pleated portions 14, 34 of the first and second web 10, 30 to the edge portion 26 of the support web 20. The edge portion 26 of the support web 30 has the same length as the non-pleated edge portions 14, 34 of the first and second web 10, 30. The support web 20 includes a tab 58 extending from the edge portion 26 outside the first and second web 10, 30. The tab 58 has a micro-hook pad 22 fixed to a planar surface 24 of the tab 58. The planar surface 24 of the tab has a portion 24' which completely surrounds the micro-hook pad 22. The portion 24' of the planar surface 24 may have a width comprised between 1-10 mm and preferably comprised between 2-7 mm.

In a possible embodiment, the support web 20 comprises a first layer 64 forming a distal portion of the tab 58 and carrying the micro-hook pad 22 and a second layer 66 forming the edge portion 26 and an intermediate portion of the tab 58 extending between said distal portion and the edge portion 26. The first layer 64 and the second layer 66 are joined to each other, for instance by a glue layer 68.

Figure 13:
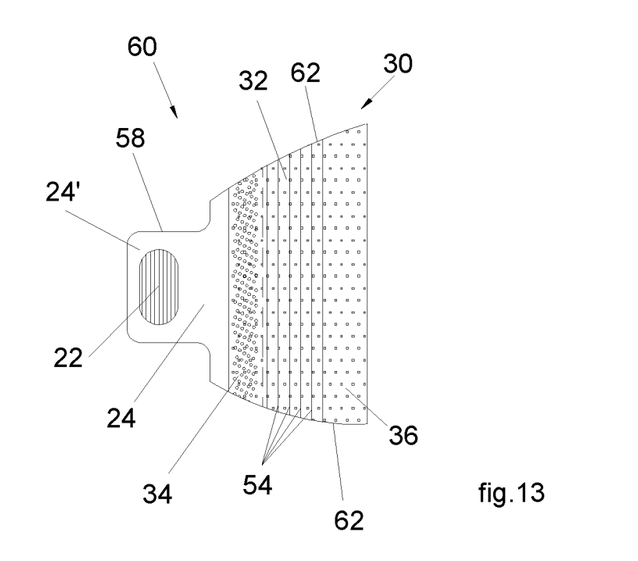
FIG. 13 is a schematic plan view showing another shape of the elastic side panel of FIG. 12.

With reference to FIG. 13, the elastic side panel 60 may have curved flanks 62, which may be formed by cutting the transversely extensible continuous elastic laminate 50 along substantially V-shaped curved cutting lines. The portion of the transversely extensible continuous elastic laminate 50 comprised between each of the two substantially V-shaped curved cutting lines is eliminated as scrap.

An absorbent sanitary article may have an absorbent central body and two or four elastic side panels 60 as previously described fixed to two opposite longitudinal edges of said central body.

As compared to the prior art disclosed in EP-A-3213728, the elastic side panel 60 according to the present invention has an increased resistance and is less exposed to the risk of breaks because the tab 58 is connected to the webs 10, 30 along the whole length of the webs 10, 30.

In use, the tabs 58 have a soft feeling to the touch because the rigid and sharp micro-hook pads 22 are completely surrounded by the web material of the support webs 20. In use the user never touches the sharp edges of the micro-hook pads 22 and does not run the risk of getting skin scratches against the sharp edges of the micro-hook pads 22.

The method for manufacturing the transversely extensible continuous elastic laminate 50 does not require the application of discrete tabs on the edges of the elastic laminate. The tabs with the respective micro-hook pads 22 are formed by applying and cutting a continuous web. This involves considerable advantages in that there is no need for complex and expensive repitch devices for applying discrete elements at a constant pitch.

Of course, without prejudice to the principle of the invention, the details of construction and the embodiments can be varied, even significantly, with respect to those illustrated here without departing from the scope of the invention as defined by the following claims.

This applies, in particular but not exclusively, to the possibility to vary as desired the shape of the micro-hook pads 22 and to the choice of the materials forming the webs. For instance, one or more of the webs 10, 20, 30 may be formed by a film of plastic material (such as polythene).

The invention claimed is:

1. A transversely extensible continuous elastic laminate comprising:
   first and second continuous webs extending along a longitudinal direction, having respective pleated central portions having pleats parallel to said longitudinal direction and respective first and second non-pleated edge portions on opposite sides of said pleated central portions,
   a continuous elastic tape extending in said longitudinal direction, and sandwiched between said pleated central portions of said first and second webs, wherein said elastic tape is elastically stretchable in a direction transversal to said longitudinal direction, and wherein said elastic tape is joined to the first and second webs by a pattern of spot welds,
   a support web including a continuous edge portion extending in said longitudinal direction, the continuous edge portion being sandwiched between said first non-pleated edge portions of said first and second webs and being fixed thereto by said pattern of spot welds, the support web including a plurality of tabs extending from the continuous edge portion outside said first and second webs, said plurality of tabs being connected to each other by said continuous edge portion and being spaced apart from each other in said longitudinal direction, each tab of the plurality of tabs having a respective micro-hook pad fixed to a planar surface of the respective tab, wherein said planar surface of each of said tabs has a portion which completely surrounds the respective micro-hook pad.

2. The transversely extensible continuous elastic laminate of claim 1, wherein adjacent micro-hook pads of each pair of pads have respective hooks oriented in opposite directions to each other.

3. The transversely extensible continuous elastic laminate of claim 1, wherein said tabs are folded over one of said first and second webs along a folding line parallel to said longitudinal direction and said micro-hook pads are releasably fastened to corresponding portions of one of said first and second webs.

4. The transversely extensible continuous elastic laminate of claim 1, wherein said support web comprises a first layer forming distal portions of said tabs and carrying said micro-hook pads, and a second layer joined to the first layer and forming said continuous edge portion and intermediate portions of said tabs extending between said distal portion and said continuous edge portion.

5. An elastic side panel for absorbent sanitary articles, comprising:
    first and second webs, having respective pleated central portions having pleats parallel to a first direction, and respective first and second non-pleated edge portions on opposite sides of said pleated central portions,
    an elastic tape sandwiched between said pleated central portions of said first and second webs, wherein said elastic tape is elastically stretchable in a second direction transversal to said first direction, wherein said elastic tape is joined to the first and second webs by a pattern of spot welds,
    a support web including an edge portion sandwiched between said first non-pleated edge portions of said first and second webs and fixed thereto by said pattern of spot welds, said edge portion having in said first direction the same length as said non-pleated edge portions, the support web including a tab extending from the edge portion outside said first and second webs, the tab having a micro-hook pad fixed to a planar surface of the tab, wherein said planar surface of said tab has a portion which completely surrounds the micro-hook pad.

6. The elastic side panel of claim 5, wherein said pattern of spot welds is reinforced in an area connecting said first non-pleated edge portions of said first and second webs to said edge portion of said support web.

7. The elastic side panel of claim 5, wherein said tab is folded over one of said first and second webs along a folding line parallel to said first direction and said micro-hook pad is releasably fastened to a corresponding portion of one of said first and second webs.

8. The elastic side panel of claim 5, wherein said support web comprises a first layer forming a distal portion of said tab and carrying said micro-hook pad, and a second layer joined to the first layer and forming said edge portion and an intermediate portion of said tab extending between said distal portion and said edge portion.

9. A method for producing the continuous transversely extensible elastic laminate according to claim 1 comprising:
    feeding two first continuous webs in a longitudinal direction, the two first continuous webs being spaced from each other in a transverse direction and having respective central portions and respective first and second edge portions on opposite sides of the respective central portions,
    feeding two continuous elastic tapes in said longitudinal direction,
    elastically stretching said two continuous elastic tapes in a direction transversal to said longitudinal direction, and applying said two continuous elastic tapes to respective central portions of said two first continuous webs while stretched in said transversal direction,
    feeding in said longitudinal direction, a continuous support web having two continuous edge portions, the continuous support web having a row of micro-hook pads fixed to a planar surface of the support web, wherein said micro-hook pads are spaced apart from each other in said longitudinal direction,
    applying said two continuous longitudinal edge portions of said support web to respective first edge portions of said two first continuous webs,
    feeding two second continuous webs in said longitudinal direction, the two second continuous webs being spaced from each other in said transverse direction, and having respective central portions and respective first and second edge portions on opposite sides of the respective central portions,
    applying said two second continuous webs to respective first continuous webs and sandwiching said two continuous elastic tapes between respective central portions of said first and second webs, and sandwiching said two continuous longitudinal edge portions of said support web between respective first edge portions of the two first and second continuous webs,
    joining to each other said two first and second webs, said two elastic tapes and the edge portions of the support web by a pattern of spot welds while said two elastic tapes are stretched in said transversal direction,
    cutting the support web along at least one continuous undulated cutting line passing between each pair of adjacent micro-hook pads so as to form two separate continuous transversely extensible elastic laminates, wherein the at least one cutting line is distanced from the edges of the micro-hook pads, so that each micro-hook pad is completely surrounded by a portion of said planar surface of said support web.

10. The method of claim 9, wherein said support web is cut by two continuous undulated cutting lines passing between each pair of adjacent micro-hook pads and forming an undulated strip of web which is removed as scrap.

11. The method of claim 9, wherein said two continuous elastic tapes have different widths in said transversal direction and/or are stretched in said transversal direction to reach different widths.

12. The method of claim 9, wherein adjacent micro-hook pads of each pair of pads have respective hooks oriented in opposite directions to each other.

13. The method of claim 9, wherein said at least one continuous undulated cutting line forms in each of said continuous transversely extensible elastic laminates a plurality of tabs connected to each other by the respective continuous longitudinal edge portion and spaced apart from each other in said longitudinal direction.

14. The method of claim 9, wherein said support web is formed by:
    unwinding from a first reel a first layer having a row of micro-hook pads applied thereon,
    unwinding from a second reel a second layer having a width in said transversal direction substantially larger than a width of said first layer, and
    joining to each other said first layer and second layer.

* * * * *

UNITED STATES PATENT AND TRADEMARK OFFICE
CERTIFICATE OF CORRECTION

| | |
|---|---|
| PATENT NO. | : 11,911,242 B2 |
| APPLICATION NO. | : 17/675227 |
| DATED | : February 27, 2024 |
| INVENTOR(S) | : Guido Bonelli and Gabriele Sablone |

It is certified that error appears in the above-identified patent and that said Letters Patent is hereby corrected as shown below:

On the Title Page (71) Applicant address information should be listed as:
- Fameccanica.Data S.p.A., San Giovanni Teatino (Chieti), ITALY -

(72) Inventor address information should be listed as:
- Guido BONELLI, San Giovanni Teatino (Chieti), ITALY
Gabriele SABLONE, San Giovanni Teatino (Chieti), ITALY -

Signed and Sealed this
Fourth Day of March, 2025

Coke Morgan Stewart
*Acting Director of the United States Patent and Trademark Office*